United States Patent
Davis et al.

(10) Patent No.: US 9,883,966 B2
(45) Date of Patent: Feb. 6, 2018

(54) FLEXIBLE SPOUT IMPROVEMENT FOR A DISPOSABLE URINAL

(71) Applicants: Zandra A. Davis, Milwaukee, WI (US); Nicole D. Young, Milwaukee, WI (US); Venus V. Dickinson, Milwaukee, WI (US); Narda N. Riley, Milwaukee, WI (US)

(72) Inventors: Zandra A. Davis, Milwaukee, WI (US); Nicole D. Young, Milwaukee, WI (US); Venus V. Dickinson, Milwaukee, WI (US); Narda N. Riley, Milwaukee, WI (US)

(73) Assignee: Ladyz By Design LLC, Wauwatosa, WI (US)

( * ) Notice: Subject to any disclaimer, the term of this patent is extended or adjusted under 35 U.S.C. 154(b) by 0 days.

(21) Appl. No.: 15/434,359

(22) Filed: Feb. 16, 2017

(65) Prior Publication Data

US 2017/0224525 A1 Aug. 10, 2017

Related U.S. Application Data

(63) Continuation-in-part of application No. 14/846,336, filed on Sep. 4, 2015, now abandoned, which is a continuation-in-part of application No. 12/135,755, filed on Jun. 9, 2008, now abandoned.

(60) Provisional application No. 60/942,512, filed on Jun. 7, 2007.

(51) Int. Cl.
A47K 11/00 (2006.01)
A61F 5/453 (2006.01)
A47K 11/12 (2006.01)

(52) U.S. Cl.
CPC .............. *A61F 5/453* (2013.01); *A47K 11/12* (2013.01)

(58) Field of Classification Search
USPC ................................................ 4/144.1–144.4
See application file for complete search history.

(56) References Cited

U.S. PATENT DOCUMENTS

| | | | |
|---|---|---|---|
| 3,000,015 A | 9/1961 | Hart | |
| 3,405,714 A | 10/1968 | Moss | |
| 3,419,913 A | 1/1969 | Crosby | |
| 3,422,463 A | 1/1969 | Lowry | |
| 3,725,962 A * | 4/1973 | Gouget | A61G 9/006 4/144.2 |
| 3,742,523 A | 7/1973 | Atkins | |
| 3,752,962 A | 8/1973 | Gauget | |
| RE28,278 E | 12/1974 | Borse | |
| 3,956,778 A | 5/1976 | Tanaka | |

(Continued)

*Primary Examiner* — Lauren Crane
(74) *Attorney, Agent, or Firm* — Joseph S. Heino (57) ABSTRACT

A urinal includes a urinal body, a urine receiving reservoir and a spout extending therefrom for receiving urine. A supplemental urinal spout is provided and comprises both an inlet portion and a retention portion, the supplemental urinal spout being attachable to the spout of the urinal to form a leak prevention seal. Opposing tabs are provided to aid in attaching the spout to the urinal. The supplemental urinal spout comprises a funnel-shaped element that is integrally formed with a cylindrical sidewall. The urinal body is preferably made of a plastic material and the supplemental urinal spout is made from a low durometer elastomeric material. The urinal and the supplemental urinal spout may be disposable.

15 Claims, 6 Drawing Sheets

(56) References Cited

U.S. PATENT DOCUMENTS

| | | | |
|---|---|---|---|
| 4,059,124 A | * | 11/1977 | Hill ........................ A61G 9/006 137/38 |
| 4,568,339 A | | 2/1986 | Steer |
| 4,994,501 A | | 2/1991 | Walsh |
| 5,235,705 A | | 8/1993 | Belisle |
| 5,331,689 A | | 7/1994 | Haq |
| 5,645,541 A | | 7/1997 | Bouser |
| 5,797,147 A | | 8/1998 | Young et al. |
| 5,839,123 A | | 11/1998 | Dunham, Sr. |
| 5,894,607 A | | 4/1999 | Van Den Berg |
| 6,021,529 A | | 2/2000 | Abbate |
| 6,021,531 A | | 2/2000 | Kirko |
| 6,070,275 A | | 6/2000 | Garlock |
| 6,119,280 A | | 9/2000 | Rentsch |
| 6,327,716 B1 | | 12/2001 | Kaus |
| 6,684,414 B1 | | 2/2004 | Rehrig |
| 7,363,661 B1 | | 4/2008 | Myers |

* cited by examiner

FLEXIBLE SPOUT IMPROVEMENT FOR A DISPOSABLE URINAL

This application is a continuation-in-part of U.S. patent application Ser. No. 14/846,336 filed Sep. 4, 2015, which is a continuation-in-part of U.S. patent application Ser. No. 12/135,755 filed Jun. 9, 2008, which claims the benefit of and priority of U.S. Provisional Patent Application No. 60/942,512 filed Jun. 7, 2007. The subject matter of each application is incorporated herein by reference.

BACKGROUND OF THE INVENTION

The present invention relates in general to urinary devices and more particularly to an improved personal urinal for collecting and storing the urine of a non-ambulatory or otherwise immobile patient. More specifically, the present invention relates to a supplemental urinal spout that combines an inlet portion with a retention portion, such retention portion not being part of the urinal reservoir but being complementary to it.

Portable male urinals for use by bed-ridden patients or people who otherwise have a need for a urinal are well known in the art. One such commonly used style of urinal includes a urine receiving reservoir for holding and/or storing urine and a spout extending from or located a distance away from the reservoir. The spout includes an inlet through which the urine is received. A cap may or may not be provided with the urinal.

A long recognized problem associated with portable male urinals is undesirable spillage of the urine following use of the urinal due to, for example, mishandling of the urinal. Backflow or spillage can result in the urine coming into contact with the patient or the bed, which in turn can cause unsanitary health conditions and result in the increased risk for further medical problems, such as infections. In addition, the workload of caretakers is increased due to the need for cleaning the patient and changing the bedding following any such spillage of urine. Bedridden patients have also been known to leave the urinal on the bed following use and then inadvertently contact it and cause it to spill.

Accordingly, numerous attempts have been made at improving portable male urinals to overcome such problems. The below-referenced U.S. patents disclose embodiments of various such urinals. The disclosures of these United States patents are hereby incorporated by reference into the present application for purposes including, but not limited to, indicating the background of the present invention and illustrating the state of the art. For example, U.S. Pat. No. 2,358,850 discloses a male urinal having a tubular trap inserted therein and connected to the urinal container by screw threads so as to minimize leakage of liquid from the container. The tubular trap must be removed before use and then reinserted following each use. Both U.S. Pat. Nos. 703,131 and 4,164,795 disclose a rotating nozzle arrangement for an inlet tube which is inserted into a urine container or collector. In both patents, rotation of the nozzle elements aids in resisting the undesired discharge of the contents of the container or collector. Backflow or spillage can still occur when attempting to place the urinal into its closed position. Spillage can also occur if the urinal is not closed after use.

In a different type of arrangement, U.S. Pat. Nos. 5,592,699 and 6,021,529 disclose devices for use in association with a urinal. These devices include a non-return valve to insure that urine can only pass in one direction, i.e. from the funnel (female urinal) or spout (male urinal) area of the device into a urine reservoir, but not out of the reservoir. The addition of a one-way valve to a urinal may appear to be a solution to the problem. However, such valves have been known to fail which, in a worst case scenario, would cause the entire reservoir contents to spill on or near the unsuspecting caregiver and/or patient. Further, the addition of a one-way valve increases the cost of the urinal, which may directly affect the decision to purchase the urinals.

Other potentially relevant patents include U.S. Pat. No. Re. 28,278, which discloses a simple disposable plastic urinal formed by a blow molding operation for use by bed-ridden patients in a hospital or the like, and U.S. Pat. No. 6,021,529 which discloses a disposable plastic urinal with a flexible extender spout and integral urine-receiving reservoir formed of blow molded plastic.

SUMMARY AND OBJECTS OF THE INVENTION

The present invention is intended to meet the above-identified needs not met by the prior art. Specifically, one aspect of the present invention provides a portable, optionally disposable, male urinal that will resist and reduce undesirable spillage of urine, particularly following use of the urinal by a patient confined to a bed.

In one aspect, according to a preferred embodiment, a portable disposable male urinal includes a urine receiving reservoir, within a urinal body, for receiving and temporarily holding the urine. The reservoir includes a handle and a removable spout extension e.g., a supplemental flexible spout attachment extending therefrom, wherein the spout has a first end with an inlet for receiving the urine and a second end designed to be secured to the reservoir by friction fit, snap fit, or by threading the attachment to the spout or other suitable means. Preferably, the spout extends upwardly at an incline from the reservoir to facilitate gravitational flow into the urinal. In one embodiment, the supplemental flexible spout is formed of a flexible bellows-type material such that the spout may be adjusted to provide a better conforming spout.

Preferably, the urinal body and the supplemental flexible spout attachment extending therefrom are formed from a plastic material. The use of a plastic material to form the urinal body and supplemental flexible spout allow for the urinal to be produced at a low cost, potentially low enough to allow the urinal to be disposable. The plastic material is preferably transparent to allow visual inspection of the quantity, clarity, and color of the urine contained in the reservoir. The urinal body may further include a drain for emptying the reservoir or withdrawing a urine specimen from the urinal. Handle means may also be provided on the urinal body to aid in the handling and transporting of the urinal.

The supplemental flexible spout attachment is preferably formed from a bendable resilient material to allow the supplemental flexible spout to be fixedly positioned at various angles. This enables the urinal of the present invention to be used more easily by a patient confined to bed while providing an increased level of protection against accidental spillage. This additional protection is provided by virtue of the supplemental flexible spout attachment providing a relatively higher and narrower opening as is provided by conventional urinals. The supplemental flexible spout attachment also helps ensure a user will not be able to confine the urine discharge to the urinal when using it.

In accordance with another aspect of the present invention, a supplemental flexible spout attachment can be used with a typical disposable urinal already in use. This permits a caregiver to provide an increase in protection against spilled urine to address recurring problems with the same patient. Because the supplemental flexible spout attachments in some embodiments are not integrally formed with the urinal, the attachment(s) can be used or not, as personal preference dictates. This will enable hospitals and nursing homes to continue purchasing and using the disposable urinals they ere most familiar with.

In accordance with another aspect of the present invention, a flexible spout attachment is provided for attachment to a typical disposable urinal of current design. This particular embodiment would provide a spout attachment that is very flexible and also fabricated of a material that is intended to prevent any injury to the user by means of scraping of skin against the inlet sidewall of the attachment. This is accomplished by using a funnel-shaped inlet having an aperture at the bottommost portion of the inlet, the inlet then being surrounded by an integrally-formed enclosure of the type that can be attached to a urinal.

In some implementations, the urinal body includes multiple flat surfaces and the generous adjustability and self-supporting functionality of the flexible supplemental spout allow for (i) supporting the urinal body on any of its multiple flat surfaces, and (ii) adjusting the flexible supplemental spout, based on the particular downwardly facing flat surface of the urinal body, to mitigate the likelihood of spillage while the urinal body rests on that particular surface.

In some implementations, the flexible supplemental spout is angularly adjustable and also can be longitudinally extended or contracted, whereby it is also lengthwise adjustable. The particular length of the flexible supplemental spout is selected based on a variety of factors, depending on the desired overall configuration of the urinal. For example, when the flexible supplemental spout is in a longitudinally contracted configuration, its length can be less than about two-thirds, one-half, or other fraction, of a length of the urinal body. Furthermore, when the flexible supplemental spout is in a longitudinally extended configuration, its length can be greater than about two-thirds, one-half, or other fraction, of a length of the urinal body.

In describing the embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected, attached, or terms similar thereto are often used. They are not limited to direct connection but include connection through other elements where such connection is recognized as being equivalent by those skilled in the art.

DESCRIPTION OF PREFERRED EMBODIMENTS

The present invention and the various features and advantageous details thereof are explained more fully with reference to the non-limiting embodiments described in detail in the following description.

Specific embodiments of the present invention will now be further described by the following, non-limiting examples which will serve to illustrate various features of significance. The examples are intended merely to facilitate an understanding of ways in which the present invention may be practiced and to further enable those of skill in the art to practice the present invention. Accordingly, the examples should not be construed as limiting the scope of the present invention.

Figure 1:
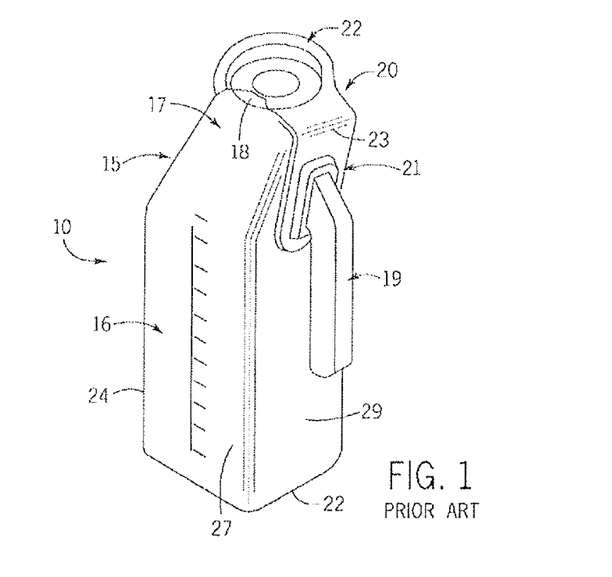
FIG. 1 is an isometric view of a conventional disposable urinal appropriately labeled "PRIOR ART."

FIG. 1 discloses a prior art disposable urinal. This urinal is described in more detail in U.S. Pat No. Re. 28,278 to Borse. In FIG. 1, a disposable urinal 10 includes a main body, or reservoir, 16, a neck, or spout, 17 extending from the upper part of the reservoir 16 and terminating in an inlet, or opening, 18 and a handle 19. A cap 20 is lockable onto the handle 19 by means of a loop 21 attached to the cap 20. The loop 21 is designed such that the handle 19 is inserted through the loop 21 prior to placing the cap 20 on the spout 18. When the cap 20 is removed from the spout 17, the cap 20 remains attached to the handle 19 via the loop 21.

The urinal 10 has a flat bottom 22 for sitting the urinal 10 in an upright position such as on a table or bed. The back side 24 of the urinal 10 is also preferably flat for the same reasons. The spout 17 preferably extends upwardly at an incline from the reservoir 16 to provide for gravitational flow of the urine from the inlet 18 into the reservoir 16.

While the prior art urinal design is widely used for male patients in hospitals and nursing homes, it does have its drawbacks. Most notable is the undesirable spillage of urine due to the mishandling of the urinal 10 or by a patient missing the urinal altogether when attempting to use the urinal 10. Mishandling of the urinal 10 may be a result of a bedridden patient leaving the urinal 10 on the bed following use and then inadvertently bumping or tipping the urinal 10 such that the patient's urine is spilled onto the patient, the bed, or even a healthcare worker. Urine spillage could result in unsanitary health conditions and the increased risk for further medical problems, such as infections. Furthermore, if urine is spilled, the bed linens need to be changed further burdening scarce healthcare resources.

Figure 2:
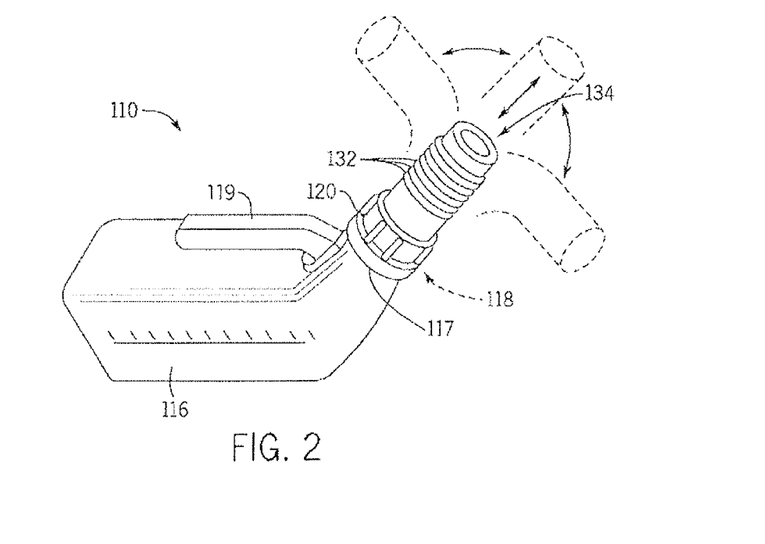
FIG. 2 is an isometric view of a first embodiment of a portable urinal with a flexible extender spout constructed in accordance with one aspect of the present invention.
Figure 3:
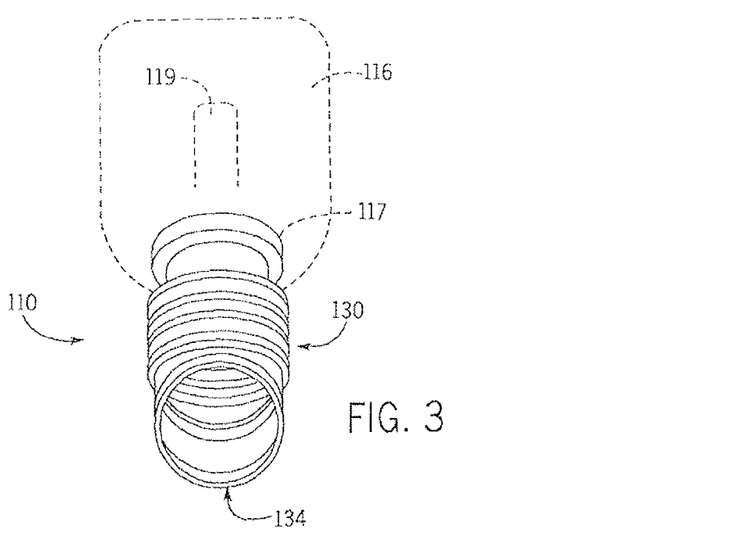
FIG. 3 is another isometric view of the portable urinal with a flexible extender spout of FIG. 2.
Figure 4:
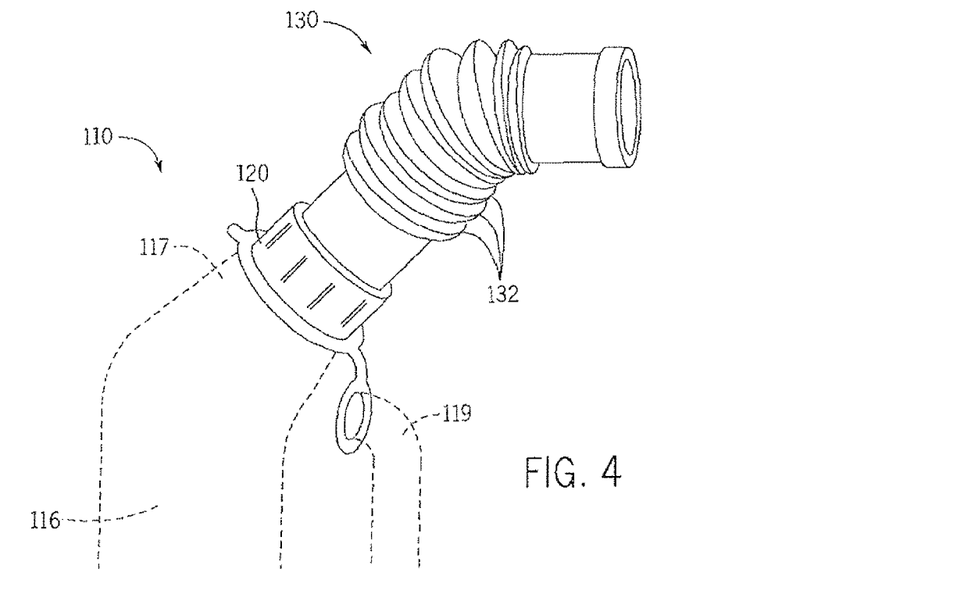
FIG. 4 is another isometric view of the urinal of FIG. 2.
Figure 5:
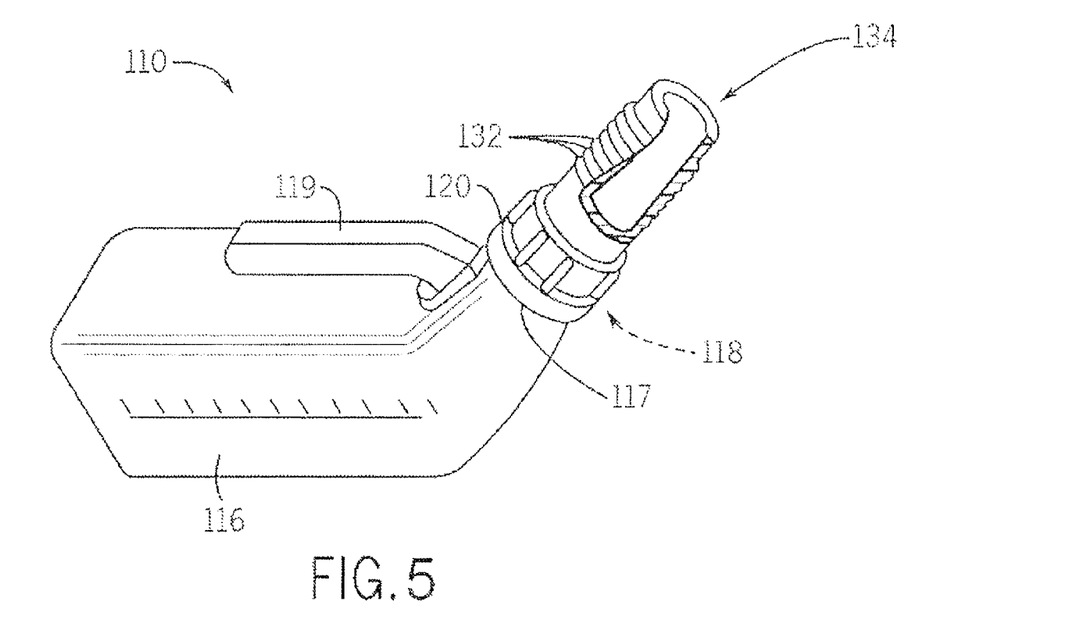
FIG. 5 is another isometric and partially sectioned view of the urinal of FIG. 2.
Figure 6:
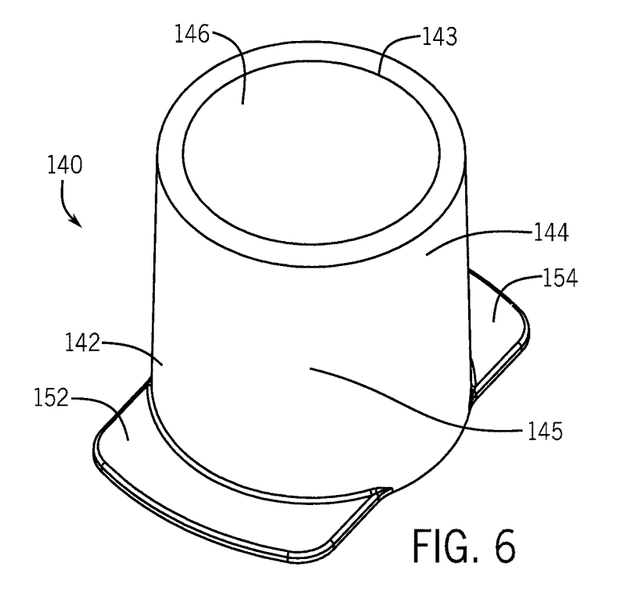
FIG. 6 is a front, side and top perspective view of an alternative preferred embodiment of a urine-receiving supplemental spout constructed in accordance with the present invention.
Figure 7:
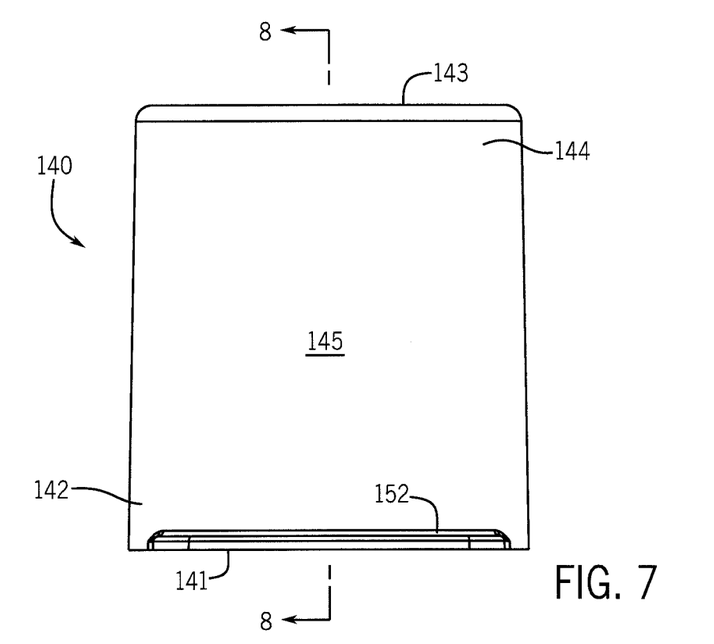
FIG. 7 is a side elevational view of the supplemental spout shown in FIG. 6.
Figure 8:
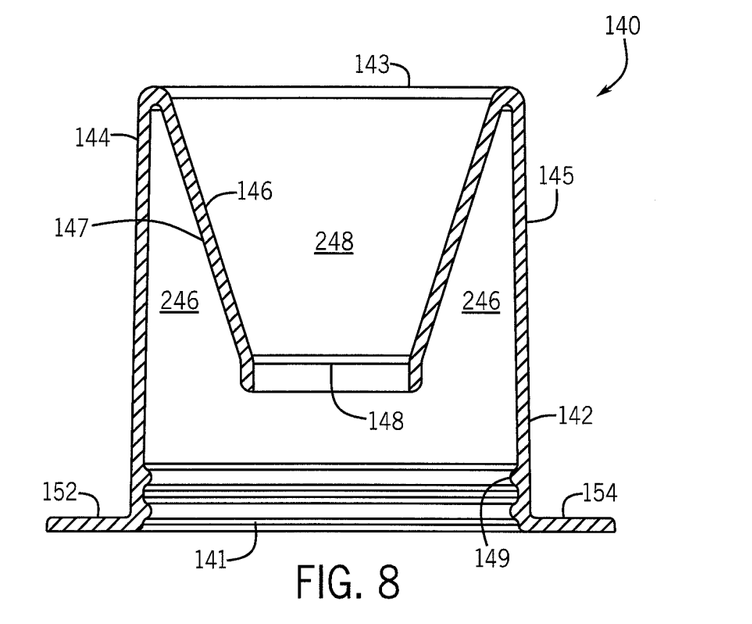
FIG. 8 is a front elevational and cross-sectioned view of the supplemental spout shown in FIGS. 6 and 7.
Figure 9:
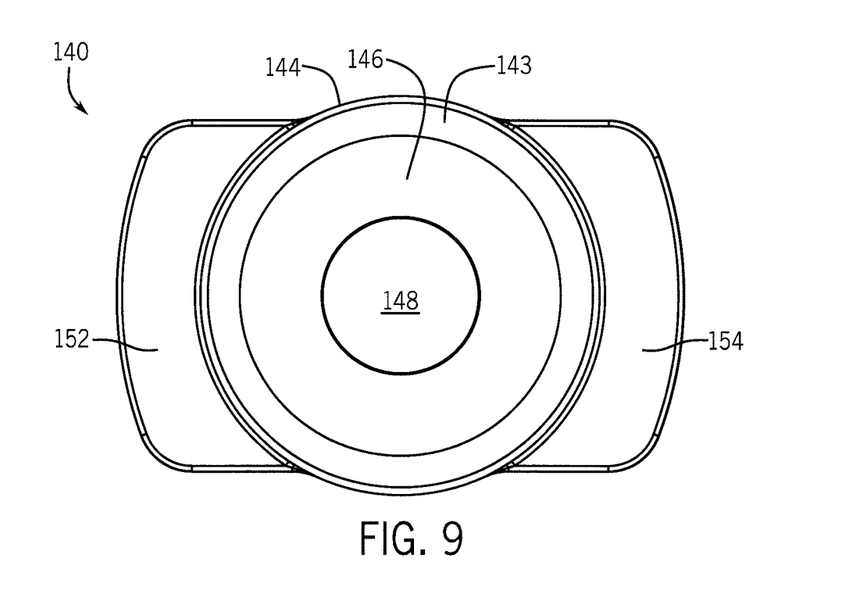
FIG. 9 is a top plan view of the supplemental spout shown in FIGS. 6 through 8.

In accordance with one aspect of the present invention, FIGS. 2-4 disclose a preferred embodiment of a portable, optionally disposable, urinal 110. Similar to the prior art urinal, the portable urinal 110 generally includes a main body portion 116 having a reservoir therein, spout 117, an opening 118, and handle 119. The body portion 116 and associated features are commonly used in hospitals and nursing homes and are available for purchase from common medical supply companies.

The urinal 110 of the preferred embodiment further includes an ancillary or supplemental spout 130 that extends from the integral reservoir spout 117, providing a flexible columnar extension therefrom. The supplemental spout 130 is designed to be placed on the integral reservoir spout 117 forming a watertight seal between the body portion 116 and supplemental spout 130. In one embodiment of the present invention, the extender spout assembly 130 is sold and marketed as an improved replacement cap for standard urinals. In another embodiment, the urinal 110 comes pre-packaged as a kit with the extender spout assembly 130.

Supplemental spout 130 is preferably formed of a bendable resilient material, for example, various suitable polymeric and/or elastomeric materials, and has a spout body portion and at least one position holding device cooperating therewith.

The position holding device(s) include a variety of structures that are capable of temporarily fixing the spout body portion in a desired use position, for example, one that is selected by the user. Exemplary of suitable holding devices for use with supplemental spout 130 include, but are not limited to, metallic, certain polymeric, or any of a variety of resilient materials that can be manipulated by a user and then hold such manipulated position or orientation for a desired use time. Such materials can be incorporated into the spout body itself, or can sleeve the outside or inside of the spout body, or otherwise axially or radially interface the spout body to facilitate its temporary fixation in a desired, self-supporting position.

In some implementations, the holding devices allow for longitudinal adjustment, e.g., provide the supplemental spout 130 with a variable length dimension. Some implementations also allow for angular adjustability, e.g., transversely with respect to a longitudinal axis of the supplemental spout 130. Such embodiments that facilitate both longitudinal and transverse adjustability of the spout 130 are seen in FIGS. 2-4.

Still referring to FIGS. 2-4, the holding devices can be implemented as, e.g., flexible ridges or bellows, 132. Each fold or segment of the ridges 132 defines a segment which can be partially or totally extended or compressed, e.g., at least partially longitudinally. In this configuration, the highly adjustable segments of ridges 132, provide continuously or infinitely variable positional adjustability to the supplemental spout 130.

In use, the flexible ridges 132 allow the supplemental spout 130 to be positioned at various angles in order to better accommodate use of the urinal 110 based upon the patient's particular needs. The ridges 132 may be formed on the exterior and/or interior of the supplemental spout 130, but preferably are formed on the exterior only with the interior remaining smooth. The smooth interior wall does not disrupt the flow of urine into the body portion 116 and thus, permits a male patient to urinate in the urinal 110 and supplemental spout 130 more comfortably. Furthermore, the supplemental spout 130 is easily grasped, further facilitating the use of the urinal 110 by a patient.

The body portion 116 and supplemental spout 130 are preferably formed of low-cost plastic material to provide for an inexpensively produced urinal 110. The preferred material also provides a flexible, yet slightly rigid structure to the body portion 116 and supplemental spout 130 so as to prevent crushing or distortion of the body portion 116 and allowing the supplemental spout 130 to remain positioned angularly for subsequent use. Preferably, the urinal 110 is transparent to provide a visual indication of the amount of urine contained within the body portion 116.

Once the urine is received in the body portion 116, the flexible extender supplemental spout 130 helps prevent the urine from flowing out of the new opening 134. One reason for this is that the extender supplemental spout 130 effectively raises the height of the opening 134. If the urinal 110 is accidentally bumped causing the urine to splash inside, the urine inside would not have enough to rise to the height of the opening 134. Furthermore, an easily opened cap (not shown) could be provided to be placed over the opening 134 of the supplemental spout 130. This increases the effective capacity of the standard urinal body portion 116, thereby requiring less frequent emptying. Once the body portion 116 is filled with urine, a caretaker can pour the urine out through the raised opening 134, rinse out the urinal 110, and return it to the patient.

Although referred to as "supplemental," it is noted that the supplemental spout 130 can actually be an integral component of the urinal 110, for example, an integral extension of, optionally in lieu of, the integral reservoir spout 117. In other words, in some embodiments of the present invention, the flexible extender supplemental spout 130 is integrally formed with the body portion 116 such that the supplemental spout 130 may not be removed from the body portion 116. The urinal of this embodiment is used in the same manner as the standard disposable urinal. When the body portion 116 has been filled with urine, a caretaker empties the urinal in a toilet through the supplemental spout 130. The urinal can then be rinsed out and returned to the patient or disposed of, at the caretaker's discretion.

Referring now to FIGS. 6-11, they show a second preferred embodiment of a urine-receiving supplemental spout, generally identified 140, that is constructed in accordance with the present invention. This supplemental urinal spout is novel in that it combines an inlet portion with a retention portion, such retention portion not being part of the urinal reservoir per se but being complementary to it. Further, the supplemental urinal spout shown is novel because it includes a funnel-shaped portion that does not extend into the urinal. Further, the supplemental urinal spout is comprised of a pliable material that provides the user with comfort in use and also allows the bottommost portion of the spout to be stretched for easy, and leakage-preventing, engagement and disengagement of the spout with an inlet of a urinal. Conveniently, the pliability of the bottommost portion of the spout allows the spout to be stretched by the user pulling two integral tabs of the spout away from one another, the tabs being integrally-formed into the spout as well. This enablement represents "tension," which is defined as a force related to the stretching of an object (and the opposite of compression). Releasing the tension placed on the tabs allows the spout to return to its original shape. See FIGS. 10 and 11 in particular.

More specifically, this embodiment of the pliable supplemental urinal spout 140 is, externally, substantially cylindrical in shape. The pliable supplemental urinal spout 140 has a bottom portion 142 and a top portion 144. The bottom portion 142 comprises a round bottom aperture 141 and the top portion 144 comprises a round top aperture 143. Extending between the bottom and top apertures 141, 143 is a continuous cylindrical side wall 145. At the top portion 144 of the supplemental urinal spout 140, a substantially funnel-shaped structure 146 is provided. The funnel-shaped structure 146 is integrally formed with the cylindrical side wall 145, the combination of which forms a unitary structure. Further, the funnel-shaped structure 146 comprises an inwardly and downwardly sloped funnel wall 147, the wall 147 comprising a conical-shaped structure extending downwardly from the top aperture 143. The funnel wall 147 terminates at a bottom funnel wall opening 148, the opening 148 being round in shape. Also formed into the bottom portion 142 of the supplemental urinal spout 140 is a lip structure 149 for removably attaching the supplemental urinal spout 140 to the portable urinal 110, of the type shown in FIG. 2, which urinal 110 generally includes a main body portion 116 having a reservoir therein, spout 117, an opening 118, and a handle 119. It is to be understood that the lip structure 149 may be attachable via snap fit, a threaded fit or any other type of fit that is configured to prevent any leakage between the supplemental urinal spout 140 and the urinal 110.

Figure 10:
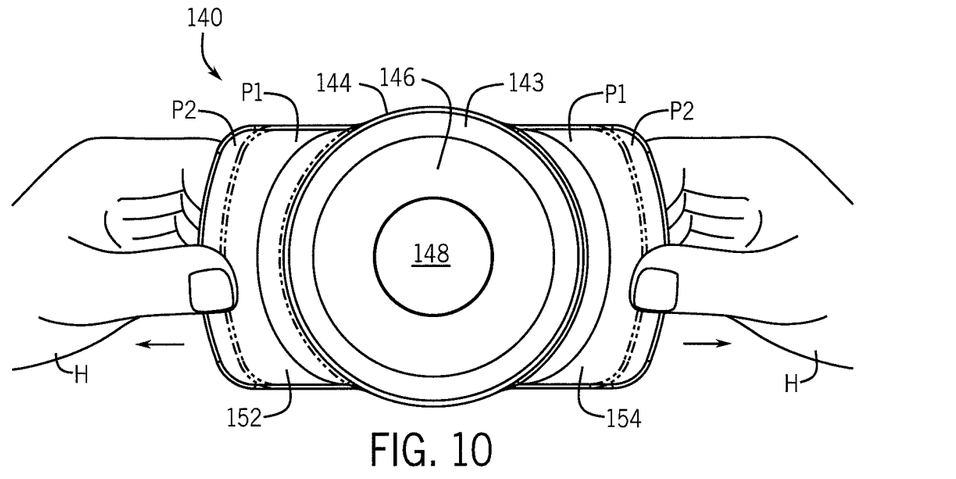
FIG. 10 illustrates a top plan view of the supplemental spout illustrating the pliability of the spout when the tabs of the spout are pulled away from one another.
Figure 11:
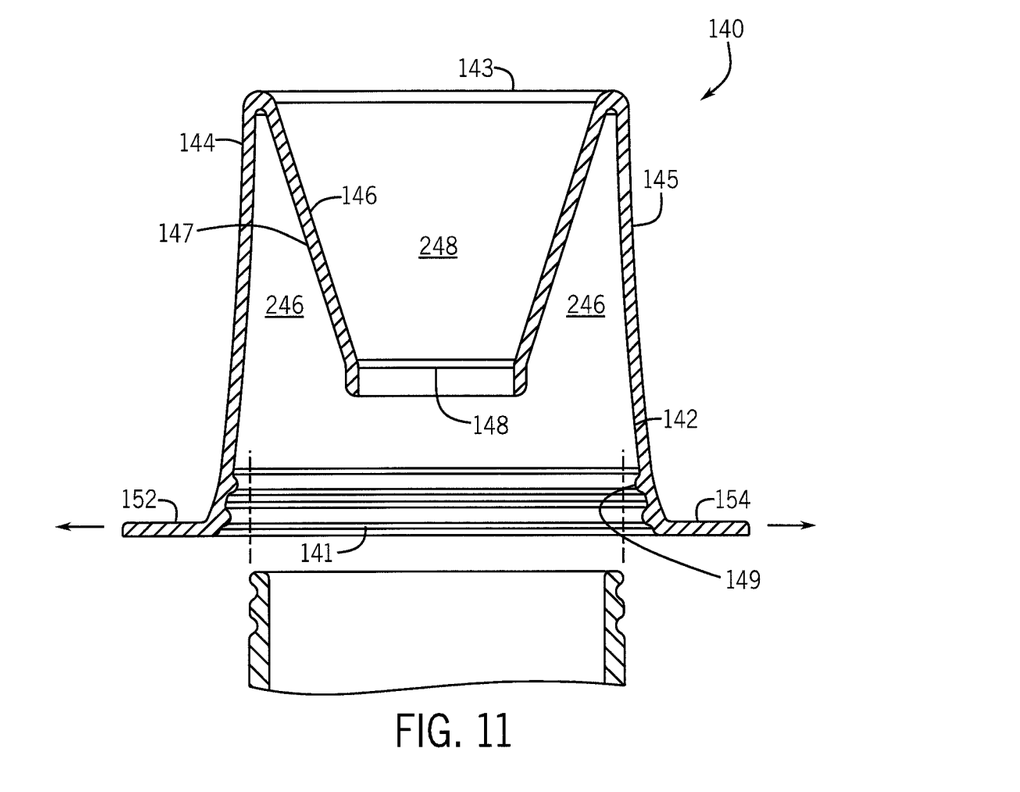
FIG. 11 is a cross-sectioned view of the spout shown in FIG. 10 prior to attachment of the spout to the neck of a urinal.

As alluded to earlier, this second preferred alternative embodiment of spout 140 is attachable to the urinal 110 because the bottom aperture 141 of the bottom portion 142 can be expanded as shown in FIGS. 10 and 11. Specifically, opposing tabs 152, 154 are provided such that the user can, by hand H, pull each of the tabs 152, 154 from a first position P1 to a second position P2. The tabs 152, 154 are coplanar and in a plane that is generally perpendicular to the axis of the supplemental urinal spout 140. In this way, the bottom portion 142 of the pliable supplemental urinal spout can be pliably stretched and expanded outwardly, as shown in both FIGS. 10 and 11, such that the lip structure 149 of the urinal spout 140 can be pulled over the engagement counterpart 159 of the urinal 150. The tabs 152, 154 must nave sufficient surface area so that each can be grasped by the user between his or her thumb and fingers.

As also alluded to earlier, in this second preferred alternative embodiment, the supplemental urinal spout 140 is made of a soft, pliable and waterproof material. In this way, the supplemental urinal spout 140, when attached to the urinal 110, can be tipped over without spillage of urine contained in it. More specifically, any urine in the urinal 110 would tend to pool in a retention portion 246 of the supplemental urinal spout 140 which lies outside the funnel-shaped structure 146 of the supplemental urinal spout 140. Accordingly, the supplemental urinal spout 140 is spill resistant. In use, the funnel-shaped structure 146 provides a soft surface against which the external male excretory organ can be placed without any risk of cut, abrasion or other injury to the organ from a hard plastic edge or the like. Further, any emission of urine into the inlet portion 248 of the supplemental urinal spout 140 that lies inside the funnel-shaped structure 146 of the supplemental urinal spout 140 will be directed downwardly toward the funnel wall opening 148, the material of the supplemental urinal spout 140 being waterproof, and then into the reservoir of the urinal 110. During use, the supplemental urinal spout 140 must be durable enough to maintain its shape, but soft enough to prevent any injury to the user of the supplemental urinal spout 140 and urinal 110 combination. The material that is used is preferably a low durometer elastomeric material, ideally on the Shore A hardness scale. That is, Shore hardness, using either the Shore A or Shore D scale, is the preferred method for determining the softness or pliability of rubbers/elastomers and is also commonly used for 'softer' plastics such as polyolefins, fluoropolymers, and vinyls. The Shore A scale is used for 'softer' rubbers while the Shore D scale is used for 'harder' ones. The hardness value is determined by the penetration of the Durometer indenter foot into the sample. Ideally, the supplemental urinal spout 140 has a Shore A hardness ranging from of from 1 to 70, preferably about 35. The softer Shore A hardness could include natural or synthetic polymers having elastic properties, e.g., rubber or other semi-rigid foam materials.

It is also to be understood that one or both of the urinal 110 and the supplemental urinal spout 140 may be disposable for purposes of avoiding contamination as may be desired or required.

Although the best mode contemplated by the inventors of carrying out the present invention is disclosed above, practice of the present invention is not limited thereto. It will be manifest that various additions, modifications, and rearrangements of the features of the present invention may be made without deviating from the spirit and scope of the underlying inventive concept. In addition, the individual components need not be fabricated from the disclosed materials, but could be fabricated from virtually any suitable materials.

It is intended that the appended claims cover all such additions, modifications, and rearrangements Expedient embodiments of the present invention are differentiated by the appended claims.

The details of the invention having been disclosed in accordance with the foregoing, we claim:

1. A male urinal comprising:
 a urinal body comprising a continuous integral sidewall, the sidewall comprising a plurality of flat surfaces for placing and supporting the urinal body on another surface, the urinal body sidewall defining a reservoir, and the urinal body reservoir further comprising an integral reservoir spout that extends from the urinal body and defines an opening in the urinal body sidewall to receive a flow of urine into the reservoir; and
 a supplemental spout that is attached directly to the integral reservoir spout of the urinal body, the supplemental spout comprising:
  a top portion comprising a round top aperture;
  a bottom portion comprising a round bottom aperture;
  a pair of opposing tabs extending from the bottom portion of the spout;
  a continuous and substantially cylindrical sidewall configured to extend between the top portion and the bottom portion;
  a substantially funnel-shaped structure extending downwardly from the round top aperture, the funnel-shaped structure being located within and integral with the sidewall, the funnel-shaped structure further comprising an inwardly tapered and downwardly extending funnel wall that does not extend beyond the round bottom aperture of the supplemental spout or into the urinal body reservoir, the funnel wall terminating in a bottom funnel wall opening;
  wherein the funnel wall forms a urine inlet portion for receiving an external male excretory organ and urine from such organ and a urine retention portion disposed between the funnel wall and the cylindrical sidewall.

2. The urinal of claim 1, wherein the supplemental spout further comprises a lip structure configured to attach the supplemental spout to the urinal body and the attachment forming a unitary leakage prevention seal.

3. The urinal of claim 2, wherein the urinal body is made from a plastic material and the supplemental spout is made from an elastomeric material.

4. The urinal of claim 3 wherein the supplemental spout is made of a elastomeric material having a durometer of between 1 and 70 on the Shore A hardness scale.

5. The urinal of claim 4 wherein the urinal body and the supplemental urinal spout are disposable.

6. A supplemental spout for use with a male urinal structure, the male urinal structure comprising a urinal body that includes multiple interconnected flat surfaces that can support the urinal body and defining a reservoir therein and a first spout that is integral with and extends from the multiple interconnected flat surfaces of the urinal body, the supplemental spout comprising:
- a top portion comprising a round top aperture;
- a bottom portion comprising a round bottom aperture;
- a pair of opposing tabs extending outwardly from the round bottom aperture;
- a continuous and substantially cylindrical sidewall extending from the top portion to the bottom portion;
- a substantially funnel-shaped structure extending downwardly from the round top aperture, the funnel-shaped structure being disposed within the sidewall and being integral with the sidewall, the funnel-shaped structure further comprising an inwardly tapered and downwardly extending funnel wall and the funnel wall terminating at a bottom funnel wall opening;
- wherein the funnel shaped structure does not extend beyond the round bottom portion of the supplemental spout and further does not extend into the urinal reservoir;
- the supplemental spout to the first spout configured for attachment of the body of the male urinal structure;
- wherein attachment of the supplemental spout to the first spout of the body of ale urinal structure forms a leak prevention seal; and
- wherein the funnel wall forms an urine inlet portion for receiving an external male excretory organ and urine from such organ and a urine retention portion disposed between the funnel wall and the cylindrical sidewall.

7. The supplemental spout of claim 6, wherein the urinal body is made from a plastic material and the supplemental spout is made from an elastomeric material.

8. The supplemental spout of claim 7 wherein the supplemental spout is made of a low durometer elastomeric material on the Shore A hardness scale.

9. The supplemental spout of claim 8 wherein the urinal body and the supplemental urinal spout are disposable.

10. A supplemental urinal spout for use with a male urinal structure, the male urinal structure comprising a urinal body that defines a reservoir and a first spout that is integral with the urinal body, the supplemental urinal spout comprising:
- a urine inlet portion for receiving an external male excretory organ and urine from such organ; and
- a urine retention portion;
- wherein the urine inlet and urine retention portions comprise:
  - a supplemental urinal spout comprising a top portion and a top aperture;
  - a tapered funnel wall extending downwardly from the top aperture, the tapered funnel wall being disposed within a sidewall of the supplemental urinal spout and being integral with the sidewall, the funnel wall further comprising a bottom funnel wall opening, the tapered funnel wall configured to not extend below the round bottom portion of the supplemental spout and further configured to not extend into the urinal reservoir; and
  - the supplemental urinal spout configured for attachment to the first spout of the body of the male urinal structure.

11. The supplemental urinal spout of claim 10 wherein the supplemental spout further comprises a bottom portion having a round bottom aperture and a lip for securing the supplemental urinal spout to the first spout of the urinal, such securement comprising a leakage prevention seal.

12. The supplemental urinal spout of claim 11, wherein the urinal body is made from a plastic material and the supplemental urinal spout is made from an elastomeric material.

13. The supplemental urinal spout of claim 10 wherein the supplemental urinal spout is made of a low durometer elastomeric material on the Shore A hardness scale.

14. The supplemental urinal spout of claim 10 wherein the urinal body and the supplemental urinal spout are disposable.

15. The supplemental urinal spout of claim 10 wherein the supplemental urinal spout is made of an elastomeric material having a durometer of between 1 and 70 on the Shore A hardness scale.

* * * * *